US007340064B2

(12) United States Patent
Onishi et al.

(10) Patent No.: US 7,340,064 B2
(45) Date of Patent: Mar. 4, 2008

(54) ACTIVE NOISE CONTROL SYSTEM

(75) Inventors: Masahide Onishi, Osaka (JP); Yoshio Nakamura, Neyagawa (JP); Toshio Inoue, Wako (JP); Akira Takahashi, Wako (JP)

(73) Assignees: Matsushita Electric Industrial Co., Ltd., Osaka (JP); Honda Giken Kogyo Kabushiki Kaisha, Tokyo (JP)

( * ) Notice: Subject to any disclaimer, the term of this patent is extended or adjusted under 35 U.S.C. 154(b) by 805 days.

(21) Appl. No.: 10/855,238

(22) Filed: May 27, 2004

(65) Prior Publication Data

US 2004/0240677 A1 Dec. 2, 2004

(30) Foreign Application Priority Data

May 29, 2003 (JP) ............................ 2003-151828

(51) Int. Cl.
*A61F 11/06* (2006.01)
*G10K 11/16* (2006.01)
*H03B 29/00* (2006.01)
*H04R 29/00* (2006.01)
*G06F 17/10* (2006.01)

(52) U.S. Cl. .................... 381/71.11; 381/56; 381/71.2; 381/71.4; 381/71.8; 708/322

(58) Field of Classification Search ............ 381/56–57, 381/71.2, 71.1, 71.4, 71.8–12, 71.3, 71.5–7; 700/28; 708/322
See application file for complete search history.

(56) References Cited

U.S. PATENT DOCUMENTS 5,455,779 A * 10/1995 Sato et al. .................. 700/280

FOREIGN PATENT DOCUMENTS

JP 06-250671 9/1994

* cited by examiner

*Primary Examiner*—Vivian Chin
*Assistant Examiner*—Douglas Suthers
(74) *Attorney, Agent, or Firm*—Jordan and Hamburg LLP

(57) ABSTRACT

An active noise control system is provided which cancels a noise using a secondary noise from a speaker that is operated in accordance with an output from an adaptive controller. The system is configured such that microphone monitor interrupts a switch to thereby stop the secondary noise from being produced, when an error signal delivered by a microphone used for an adaptive computation in an LMS processing portion has the same sign for a predetermined duration. This allows the system to prevent the user from hearing an abnormal acoustic noise resulting from an abnormal operation or divergence of an adaptive filter even when the output signal from the microphone used for the adaptive computation is indicative of an abnormal level.

2 Claims, 6 Drawing Sheets

ACTIVE NOISE CONTROL SYSTEM

The present disclosure relates to subject matter contained in priority Japanese Patent Application No. 2003-151828, filed on May 29, 2003, the contents of which is herein expressly incorporated by reference in its entirety.

BACKGROUND OF THE INVENTION

1. Field of the Invention

The present invention relates to an active noise control system which produces a signal that is interfere with and attenuates an uncomfortable noise generated in the passenger compartment of a vehicle by the operation of the engine or under the running condition thereof, the signal being equal in amplitude and opposite in phase with the noise. More particularly, the present invention is directed to an active noise control system which prevents an abnormal acoustic noise from being generated due to an improper noise reduction operation resulting from an abnormal output signal from a microphone for sensing a residual noise level.

2. Description of the Related Art

Conventionally known in the prior art is a method for sensing the abnormal level of an active noise control system using an output signal from the active noise control system and a signal obtained in accordance with the behavior of a speaker for radiating the output signal into the air (e.g., see Japanese Laid-Open Patent Publication No. Hei 6-250671). FIG. 6 is a view illustrating the configuration of a conventional active noise control system disclosed in Japanese Laid-Open Patent Publication No. Hei 6-250671.

The active noise control system shown in FIG. 6 operates to cancel a noise released through a muffler from an engine or a noise source. A controller portion 9 produces a noise-canceling signal, which is in turn converted from digital to analog at a D-A (Digital to Analog) converter 4 and then filtered through a low-pass filter 3 to remove unwanted high frequency harmonic components therefrom, finally supplied to a power amplifier 2. The noise-canceling signal that has been power amplified at the power amplifier 2 is radiated through a speaker 1 into the air as an acoustic canceling-signal, which is then interfere with and cancels the noise from the muffler. The cancellation may result in a residual noise, which is then converted by a microphone 5 into an electric signal to be supplied to an amplifier 6 as an error signal. The error signal that has been amplified at the amplifier 6 is filtered through a low-pass filter 7 to remove unwanted high frequency harmonic components therefrom, and then supplied to an A-D (Analog to Digital) converter 8. The A-D converter 8 converts the supplied analog signal into a positive or negative digital signal with respect to an initial voltage setting (e.g., the DC bias voltage for the low-pass filter 7) employed as a reference value (0). The error signal "e" that has been quantized and converted from analog to digital at the A-D converter 8 is supplied to the controller portion 9 to produce a noise-canceling signal. The controller portion 9 incorporates a DSP (Digital Signal Processor) or a discrete micro-processing unit for processing digital signals. The DSP is provided with an adaptive filter for performing main processing, in which the noise-canceling signal is adaptively produced in accordance with a noise demonstrative signal (reference signal) resulting from the pulsation frequency of the engine and the error signal, thereby making it possible to reduce a stationary low-frequency noise generated by the noise source.

The active noise control system is provided with an abnormal level detection portion 13 for sensing its own abnormal level. The abnormal level detection portion 13 is supplied with abnormal level detection signals delivered from each portion of the active noise control system. When processing these abnormal level detection signals to find an abnormal level, the abnormal level detection portion 13 produces a signal for resetting the controller portion 9, a signal for reducing the level of the acoustic canceling-signal, and a signal for turning off a power supply switch 14 of the controller portion 9 itself, thereby stopping the function of producing the noise-canceling signal.

Now, the abnormal level detection signal for the abnormal level detection portion 13 to sense the abnormal level of the active noise control system itself will be described in more detail below. The abnormal level detection signal shown by (1) in FIG. 6 serves to sense the abnormal level based on a strong vibration of the diaphragm of the speaker 1. A large vibrational amplitude of the diaphragm causes a switch, which is provided on the reverse side of the diaphragm of the speaker 1, to be turned on or off to produce a signal, which is then compared with the reference signal, thereby sensing the abnormal level. That is, the abnormal level can be sensed because the large vibrational amplitude of the diaphragm of the speaker 1 means that the active noise control system is delivering an excessive output level.

The abnormal level detection signal shown by (2) in FIG. 6 serves to sense the abnormal level in accordance with an abnormal increase in temperature of the voice coil of the speaker 1. The speaker 1 is provided with a thermocouple near the voice coil to produce a signal resulting from a thermo-electromotive force being converted into a voltage, and the signal is compared with a reference voltage, thereby sensing the abnormal level. That is, the abnormal level can be sensed because an abnormal increase in temperature of the voice coil means that an excessive output signal current is flowing.

The abnormal level detection signal shown by (3) in FIG. 6 serves to sense the abnormal level in accordance with a change in magnetic flux density caused by an output current from the power amplifier 2 to the speaker 1. A magnetic flux density detector is provided on a cable through which the output current flows to the speaker 1, and the output signal from the magnetic flux density detector is rectified and smoothed to produce a signal, which is in turn compared with the reference voltage to thereby sense the abnormal level. That is, the abnormal level can be sensed because detecting a change in magnetic flux density means that an abnormal low-cycle current of a high output level is flowing through the speaker 1.

The abnormal level detection signal shown by (4) in FIG. 6 serves to sense the abnormal level in accordance with the level of the noise-canceling signal to be supplied to the power amplifier 2. The output signal from the low-pass filter 3 to be supplied to the power amplifier 2 is branched to produce a rectified and smoothed signal, which is in turn compared with the reference voltage to thereby sense the abnormal level. That is, the abnormal level can be sensed because the noise-canceling signal level indicative of an abnormal value means that the expected maximum value is exceeded.

The abnormal level detection signal shown by (5) in FIG. 6 serves to sense the abnormal level in accordance with the level of a signal produced by removing the noise-canceling signal from the signal to be supplied to the power amplifier 2. The output signal from the low-pass filter 3 to be supplied to the power amplifier 2 is branched and then allowed to pass through a band-stop filter for removing the frequency band of the noise-canceling signal, thereby providing a band-stop signal. The band-stop signal is rectified and smoothed to produce a signal, which is in turn compared with the reference voltage to thereby sense the abnormal level. That is, the abnormal level can be sensed because the band-stop signal level indicative of an abnormal value means that frequency components other than those of the noise-canceling signal are contained.

The abnormal level detection signal shown by (6) in FIG. 6 serves to sense the abnormal level through the phase comparison between a signal to be supplied to the power amplifier 2 and the output signal from the low-pass filter 7. The abnormal level is sensed in accordance with the level of an output signal from a phase comparator which compares the phase of a signal branched from the output signal from the low-pass filter 3 to be supplied to the power amplifier 2 and the phase of the output signal from the low-pass filter 7. That is, the abnormal level can be sensed because the level of the output signal from the phase comparator indicative of an abnormal value means that the signals no longer hold the relationship of being equal in frequency and opposite in phase.

However, the conventional active noise control system allows the controller portion 9 to stop the function of producing the noise-canceling signal as a result of the speaker 1 or the power amplifier 2 having already operated, or after the abnormal level has been determined in accordance with the value of the noise-canceling signal that has been already delivered as a signal. The system allows the abnormal acoustic noise to continually radiate into the air for the period of time immediately after the abnormal level has actually occurred until the abnormal level detection portion 13 determines the abnormal level. Accordingly, the conventional system may cause the user to possibly hear the abnormal acoustic noise during that period of time. Particularly, when the error signal "e" from the microphone 5 to be supplied to the controller portion 9 is indicative of the abnormal level, the controller portion 9 adaptively computes an abnormal level, providing an improper noise reduction effect. Additionally, in the worst case, it is highly possible that the computed result of the adaptive filter does not converge but diverges. In this case, until the abnormal level detection portion 13 determines the abnormal level, an output signal having an approximately maximum level that the controller portion 9 can possibly provide is delivered successively. Thus, the conventional system may cause significant discomfort to the user.

SUMMARY OF THE INVENTION

The present invention is to overcome the aforementioned problems. It is therefore the object of the present invention to provide an active noise control system which prevents the user from hearing an abnormal acoustic noise from an adaptive controller even when an output signal from a microphone used for adaptive computations is indicative of an abnormal level.

An active noise control system according to the present invention includes, among other things, microphone monitor for stopping a secondary noise being produced from an adaptive controller when output signals delivered by a microphone to be supplied to the adaptive controller have the same positive or negative sign for a predetermined duration. This feature allows for sensing an abnormal level indicative of the output signal from the microphone fluctuating not alternately but directly, and accordingly stopping the secondary noise from being generated.

Another active noise control system according to the present invention includes, among other things, microphone monitor for stopping a secondary noise being produced from an adaptive controller when the ratio between a duration of the positive sign of output signals delivered by the microphone to be supplied to the adaptive controller and that of the negative sign thereof is greater than or equal to a predetermined value. This feature allows for sensing an abnormal level indicative of the output signal from the microphone having changed to be biased off zero at a DC offset, thereby making it possible to accordingly stop the secondary noise from being generated.

While novel features of the invention are set forth in the preceding, the invention, both as to organization and content, can be further understood and appreciated, along with other objects and features thereof, from the following detailed description and examples when taken in conjunction with the attached drawings.

DETAILED DESCRIPTION OF THE PREFERRED EMBODIMENTS

First Embodiment

Now, the present invention will be explained below in accordance with an active noise control system according to a first embodiment. In the figures, the same components as those of the conventional active noise control system described in relation to the related art are indicated by the like reference symbols and will not be discussed repeatedly. By way of example, the present invention will be described in accordance with the active noise control system incorporated into a vehicle to reduce a vibrational noise in the passenger compartment caused by the operation of the engine of the vehicle under running conditions.

Figure 1:
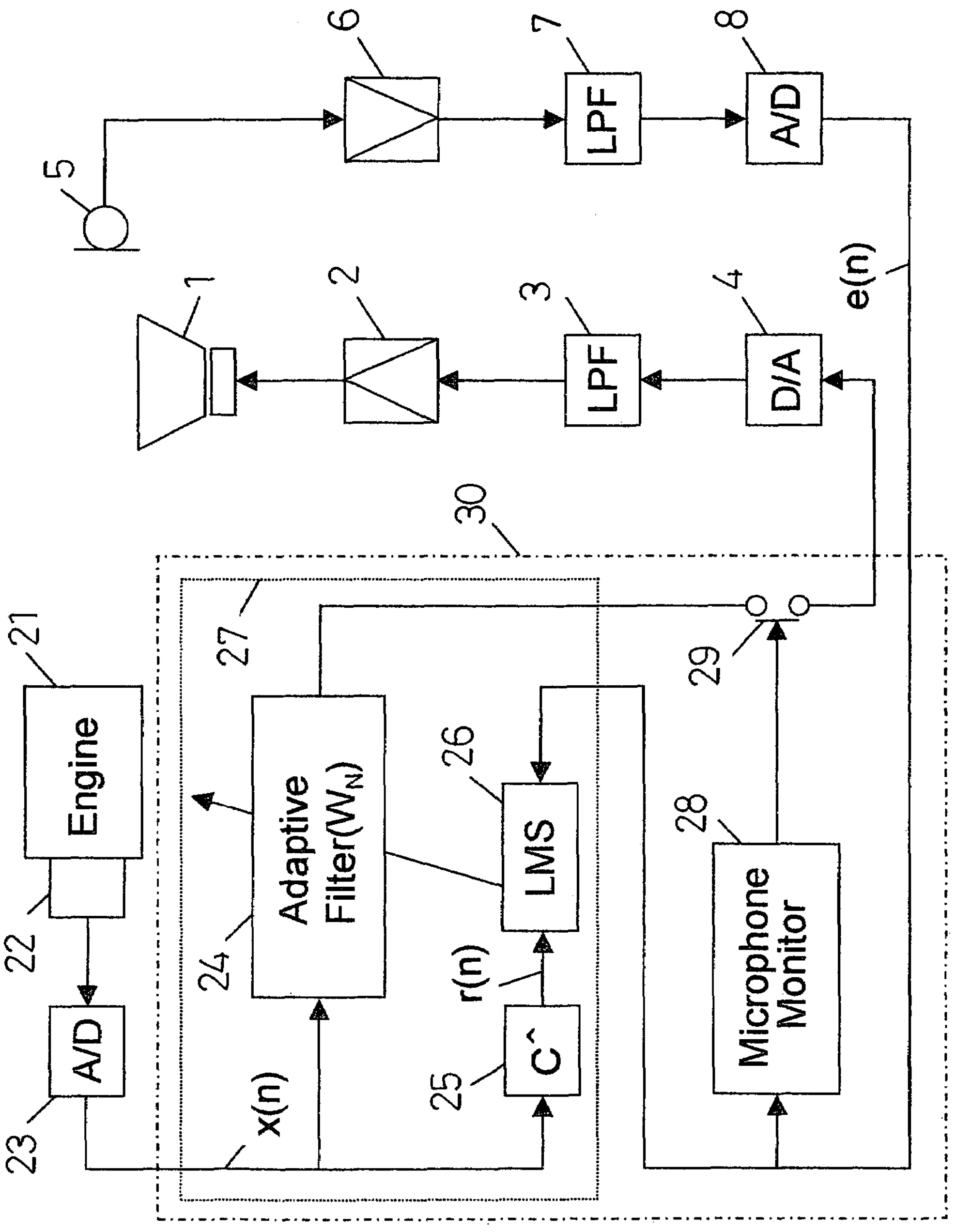
FIG. 1 is a block diagram illustrating the configuration of an active noise control system according to a first embodiment of the present invention.

FIG. 1 illustrates in a block diagram form the configuration of the active noise control system according to the first embodiment. Referring to FIG. 1, with an engine 21 being a noise source that generates a problematic noise, the active noise control system generates a secondary noise for reducing a vibrational noise caused by the engine 21 and emitted into the passenger compartment.

To obtain a signal having a high correlation with the vibrational noise generated by the engine 21, a vibration sensor 22 is provided near the engine 21 to sense mechanical vibrations produced by the engine 21. The output signal from the vibration sensor 22 is quantized and converted into a digital signal at an A-D converter 23, and then supplied as a reference signal "x" to an adaptive controller 27 that is incorporated into a DSP 30 serving as a discrete microprocessing unit.

The adaptive controller 27 includes an FIR (Finite Impulse Response) adaptive filter 24 (with a filter coefficient $W_N$) having N updatable taps and an FIR compensation filter 25 (with a filter coefficient C^) for compensating a delay in signal transmission from the output of a D-A converter 4 to the input of an A-D converter 8. The adaptive controller 27 also includes an LMS processing portion 26 which updates the filter coefficient $W_N$ of the adaptive filter 24 so as to minimize an error signal "e" in accordance with the LMS (Least Mean Square) algorithm using a reference signal "r" filtered through the compensation filter 25 and the error signal "e" or a digitized version of a signal provided by a microphone 5 sensing the residual noise resulting from the interference between the problematic noise and the secondary noise.

The reference signal "x" supplied to the adaptive controller 27 is integrated by convolution with the filter coefficient $W_N$ of the adaptive filter 24 to form the secondary noise to cancel the problematic noise. Then, the secondary noise passes through the D-A converter 4 and a low-pass filter 3 to be released into the passenger compartment from a speaker 1 via a power amplifier 2 serving as secondary noise generator. As a signal highly correlated with the vibrational noise generated by the engine 21, it is also possible to use a TDC (top dead center) sensor output signal or a tachometer pulse.

As described above, this active noise control system generates the secondary noise by updating the filter coefficient $W_N$ of the adaptive filter 24 so as to minimize the error signal "e" or an output signal delivered by the microphone 5 to be supplied to the adaptive controller 27. It can be thus seen that the error signal "e" is an extremely critical signal to allow the active noise control system to properly function. The error signal "e" indicating an abnormal level for some reason due to the microphone 5 or an amplifier 6 would not only cause the noise reduction effect to be improperly obtained but also the filter coefficient $W_N$ of the adaptive filter 24 to diverge, resulting in an abnormal acoustic noise being generated from the speaker 1 at the worst. Therefore, the error signal "e" indicative of the abnormal level has to be immediately sensed to stop generating the secondary noise before the filter coefficient $W_N$ of the adaptive filter 24 takes an abnormal value to diverge.

To this end, the first embodiment provides for microphone monitor 28 in the DSP 30 and a switch 29 that is controllably turned on or off by the microphone monitor 28. The error signal "e," which is supplied to the adaptive controller 27, is also branched to the microphone monitor 28, which in turn monitors a change in sign of the signal all the times to know whether the signal has changed alternately. When supplied error signals "e" have the same sign successively for a predetermined duration, the microphone monitor 28 senses an abnormal level indicative of not an alternate change but a direct change in the error signal "e." The microphone monitor 28 then immediately interrupts the switch 29, thereby preventing the secondary noise, adaptively computed using the abnormal error signal "e," from being radiated from the speaker 1. These microphone monitor 28 and the switch 29 are implemented in the form of software in the DSP 30.

Figure 2:
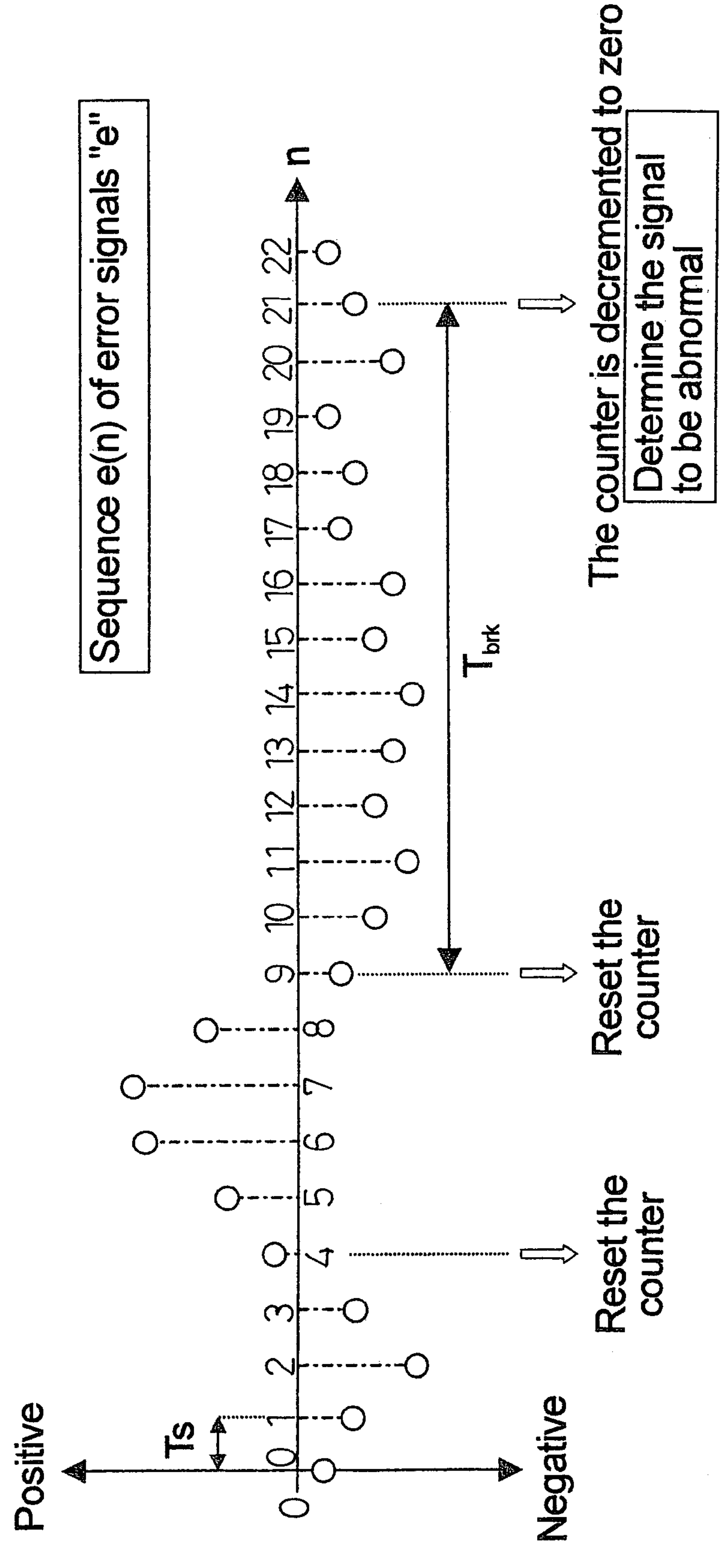
FIG. 2 is a view illustrating the sequence of error signals according to the first embodiment.
Figure 3:
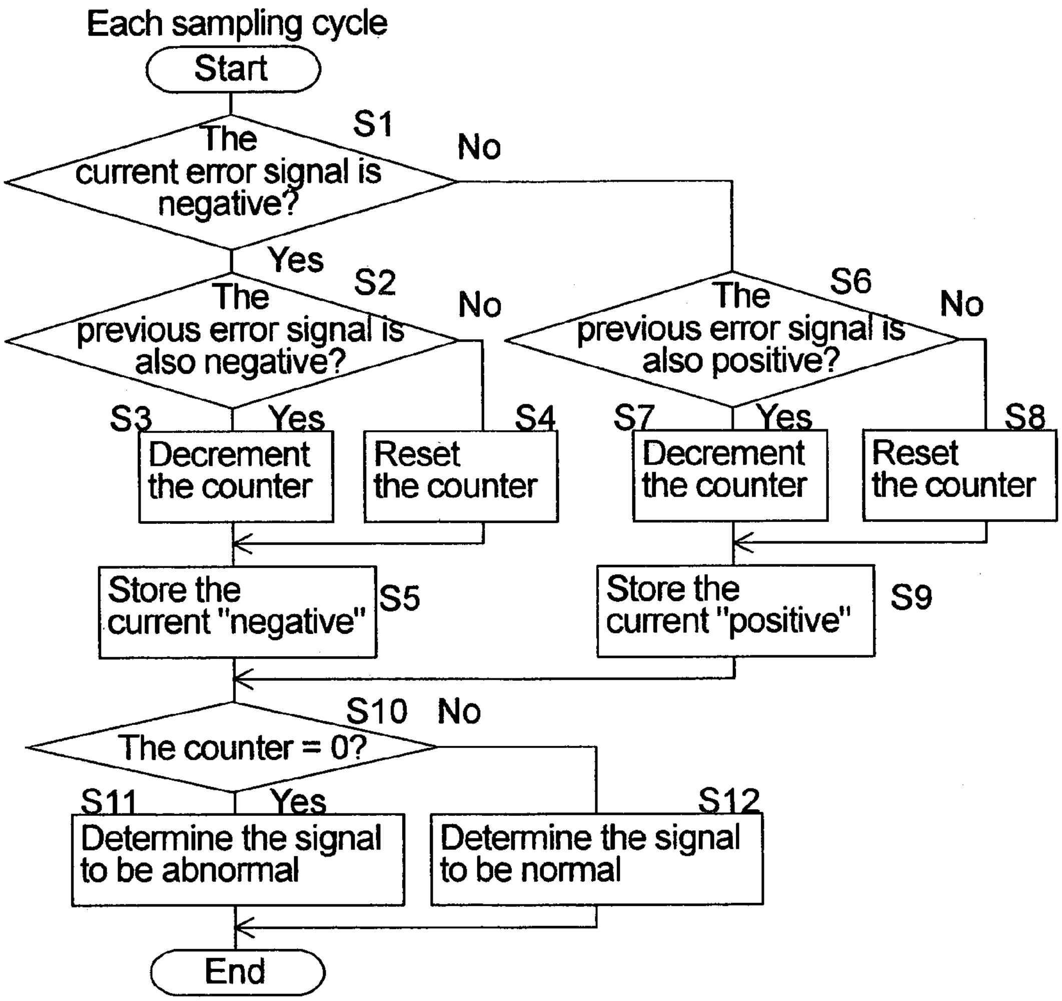
FIG. 3 is a flowchart according to the first embodiment.

Referring to FIGS. 2 and 3, an explanation is given below to the microphone monitor 28 monitoring changes in sign of the error signal "e."

FIG. 2 graphically shows an exemplary sequence {e(n)} of error signals "e" that are quantized at sampling cycle Ts (sec) intervals from time "0" (n=0) at which the A-D converter 8 starts operating after the active noise control system has been activated. Every time the value of the error signal "e" is updated or at every sampling cycle Ts (sec), the microphone monitor 28 determines whether the sign of the error signal "e" during the current sampling interval is the same as that of the error signal "e" during the previous sampling interval. The microphone monitor 28 is provided therein with a (down-count) counter to measure the duration in which the error signals "e" take on the same sign. The counter is reset to an initial value K at n=0. Thereafter, at each sampling cycle of n=1, 2, 3 and so on, if the sign of the error signal "e" during the current sampling interval is the same as that of the error signal "e" during the previous sampling interval, the counter is decremented by one. If the sign of the error signal "e" during the current sampling interval is different from that of the error signal "e" during the previous sampling interval, the initial value K is re-set to the counter (to be initialized).

The initial value K set to the counter is determined as follows. That is, if the microphone monitor 28 is allowed to detect an abnormal level when the signs of the error signals "e" are the same for a duration of $T_{brk}$ (sec), then $K=T_{brk}/Ts=T_{brk}\cdot fs$, where fs is the sampling frequency. If the error signal "e" takes on an abnormal level for some reason to have the same sign successively in the subsequent intervals, the counter continues to be decremented. As a result, the counter will be decremented eventually to zero, which is equivalent to the error signals "e" having the same sign for a duration of $T_{brk}$ (sec). Accordingly, the microphone monitor 28 determines at every sampling cycle whether the counter indicates zero, thereby making it possible to sense an abnormal level of the error signal "e" changing directly.

The example shown in FIG. 2 is adapted such that the microphone monitor 28 senses an abnormal level when the error signal "e" has the same sign for a duration of 12×Ts (sec). That is, since $T_{brk}=12\cdot Ts$ (sec), the counter is set at an initial value K=12. First, at n=0, the microphone monitor 28 stores the sign of error signal e(0) being negative, while the counter is initialized. At n=1, since the sign of error signal e(1) is negative or the same as the sign of e(0), the counter is decremented. As a result, the counter indicates "11"; however, since it is not equal to zero, the error signal "e" is determined to be normal. Subsequently in the similar manner, at n=2 and 3, since the sign of the error signal "e" is negative, the counter is decremented but only to "9"; the error signal "e" is thus determined to be normal during these intervals.

Now, at n=4, since error signal e(4) has changed to have the positive sign, the counter is again initialized. Subsequently in the similar manner, at n=5, 6, 7, and 8, since the sign of the error signal "e" is positive, the counter is decremented but only to "8"; the error signal "e" is thus determined to be normal during these intervals. Now, at n=9, since error signal e(9) has changed to have the negative sign again, the counter is again initialized. Subsequently in the similar manner, at n=10, 11, . . . , 21, and 22, since the sign of the error signal "e" is negative, the counter is decremented, and eventually to "0" at n=21. At this time, the microphone monitor 28 detects that the error signal "e" has the same sign for a duration of $T_{brk}$ (sec) from n=9, thereby sensing the abnormal level indicative of direct changes.

FIG. 3 is a flowchart showing the microphone monitor 28 operating at every sampling cycle. First, at step s1, the sign of the error signal "e" during the current sampling interval is determined. If the sign of the error signal "e" during the current sampling interval is negative, the process determines in step s2 whether the sign of the error signal "e" during the previous sampling interval is also negative. If the sign of the error signal "e" during the previous sampling interval is also negative, the sign of the error signal "e" has been successively negative, and thus the process decrements the counter in step s3. If the sign of the error signal "e" during the previous sampling interval is positive, the sign of the error signal "e" has changed from positive to negative, and thus the process initializes the counter in step s3.

Then, for use during the next sampling interval, the sign of the error signal "e" during the current sampling interval being negative is stored in step s5. Likewise, if the sign of the error signal "e" during the current sampling interval is positive, the process determines in step s6 whether the sign of the error signal "e" during the previous sampling interval is also positive. If the sign of the error signal "e" during the previous sampling interval is positive, the sign of the error signal "e" has been successively positive, and thus the process decrements the counter in step s7. If the sign of the error signal "e" during the previous sampling interval is negative, the sign of the error signal "e" has changed from negative to positive, and thus the process initializes the counter in step s8. Then, for use during the next sampling interval, the sign of the error signal "e" during the current sampling interval being positive is stored in step s9.

Now, in step s10, the process determines whether the counter, which changed its value in steps s3, s4, s7, and s8, has changed to zero. If the counter has not changed to zero, the process determines in step s12 that the error signal "e" is normal. If the counter has changed to zero, the process senses an abnormal level in step s11 because the sign of the error signal "e" is the same for a duration of $T_{brk}$ (sec), allowing the microphone monitor 28 to interrupt the switch 29.

The first embodiment is directed to canceling a vibrational noise in the passenger compartment generated by the operation of the engine under the running condition of the vehicle. In general, the spectral distribution of such vibrational noise contains closely spaced components in the relatively low frequency region, and many passengers may feel uncomfortable in the passenger compartment with noise particularly at frequencies of 100(Hz) or lower. To control such low frequencies, the adaptive controller 27 may have a relatively long computing cycle or sampling cycle Ts (sec), with the sampling frequency fs being typically set at 3 (kHz). The microphone 5 is surrounded by acoustic signals of various frequencies, including external disturbances such as road and wind noises or musical sounds played in the passenger compartment, in addition to the problematic noises and the secondary noise from the speaker 1. This would cause a normal error signal "e" to vary alternately. Therefore, the duration $T_{brk}$ for sensing the abnormal level of the error signal "e" varying not alternately but directly can be well set at the order of $T_{brk}$=1 (sec). In this case, the counter is set at initial value K=3,000.

As described above, to stably reduce noises in the passenger compartment with external disturbances always present, it is necessary to provide lower settings to the adaptive convergence coefficient of the LMS processing portion 26. This allows the process to perform adaptive computations relatively slowly. Accordingly, when the abnormal level occurs in the error signal "e", even a setting of around $T_{brk}$=1 (sec) would allows the switch 29 to be well interrupted before the adaptive filter 24 is brought into divergence, thereby preventing the passenger from hearing an abnormal acoustic noise resulting from the divergence.

As described above, the active noise control system according to the first embodiment is designed such that when the sign of an error signal from the microphone employed for adaptive computations is identical for a predetermined duration, the process senses the abnormal level of the error signal varying not alternately but directly to then stop generating the secondary noise. This prevents the user from hearing an abnormal output acoustic noise from the adaptive controller.

Second Embodiment

Now, the present invention will be explained below in accordance with another active noise control system according to a second embodiment. The second embodiment is configured in the same manner as the first embodiment shown in FIG. 1, being different therefrom only in the microphone monitor 28 employing a different algorithm for sensing an abnormal level. In the second embodiment, when the ratio between the duration of the positive sign of the error signal "e" supplied to the microphone monitor 28 and that of the negative sign thereof is greater than or equal to a predetermined value, the process senses an abnormal level indicative of the error signal "e" having changed to be biased off zero at a DC offset. Then, the process immediately interrupts the switch 29, thereby preventing a secondary noise produced by an adaptive computation using an abnormal error signal "e" from being radiated out of the speaker 1.

Figure 4:
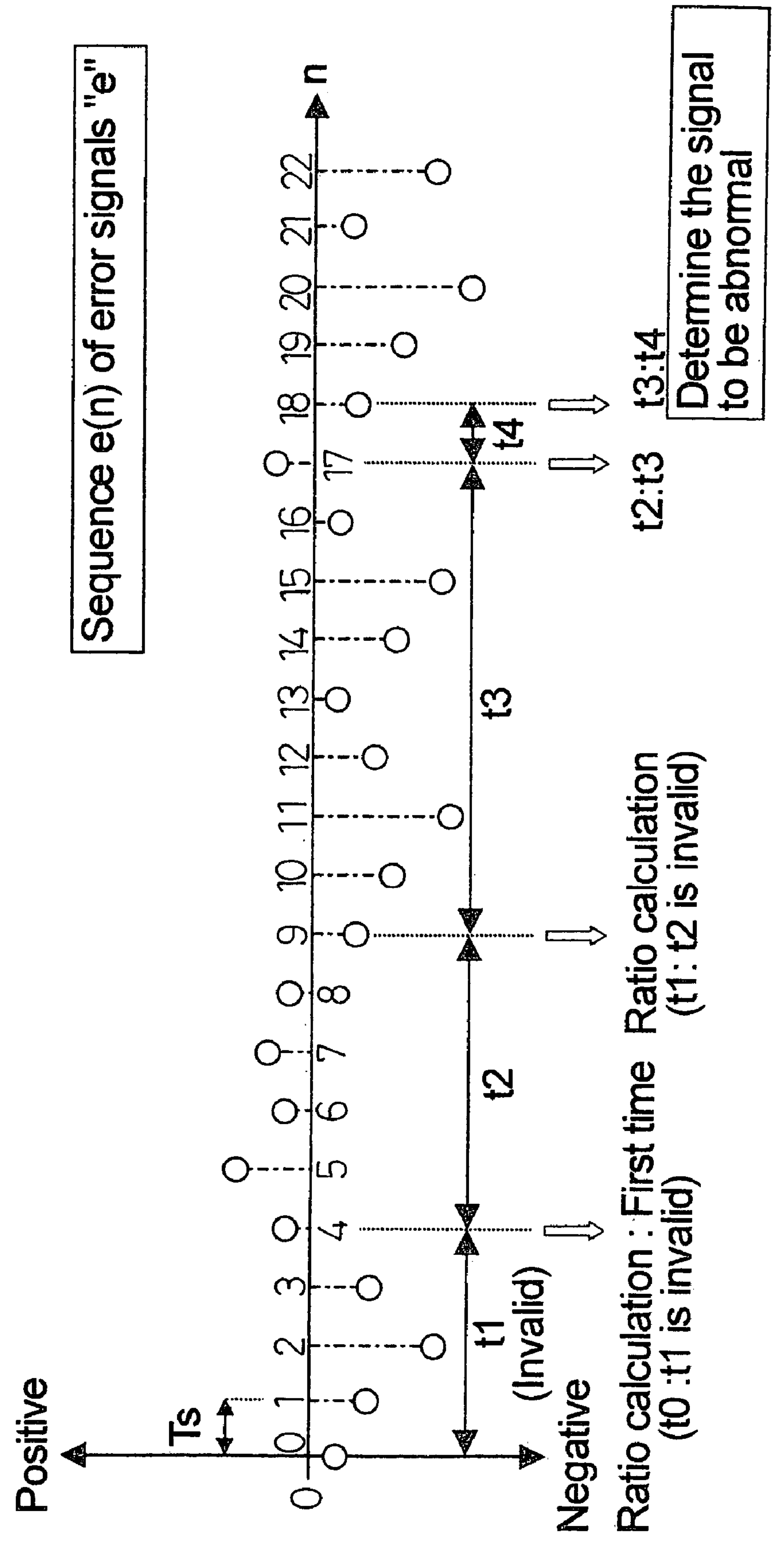
FIG. 4 is a view illustrating the sequence of error signals according to a second embodiment.
Figure 5:
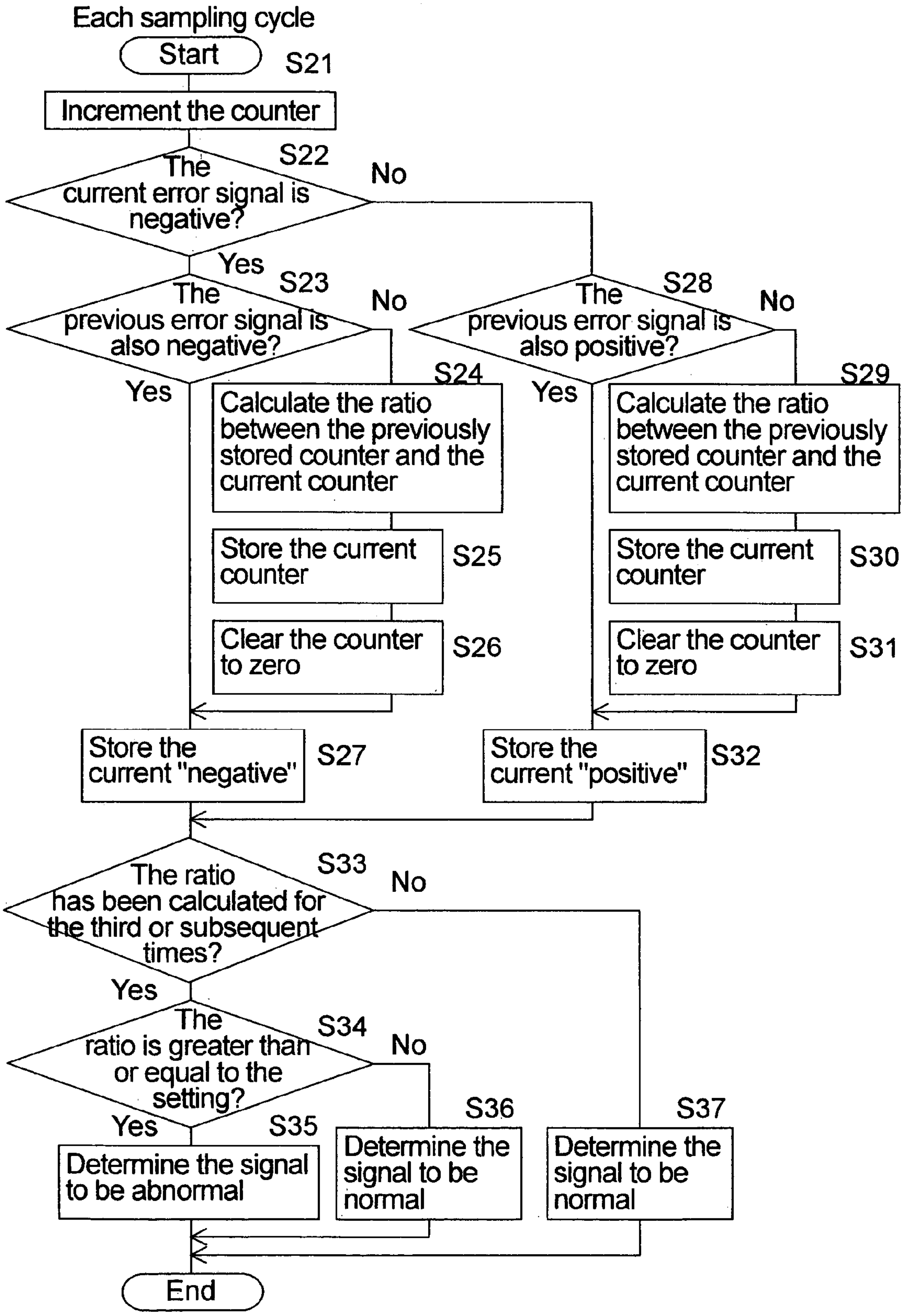
FIG. 5 is a flowchart according to the second embodiment.
Figure 6:
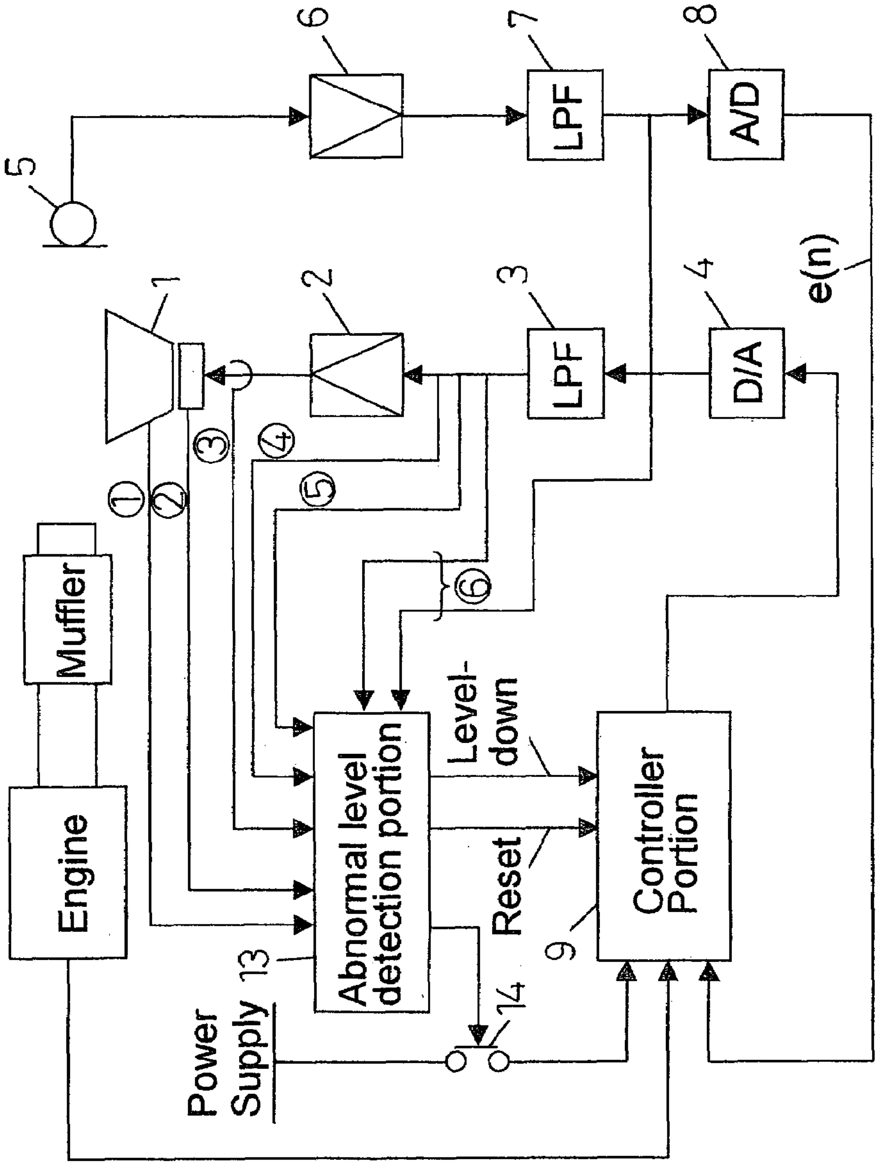
FIG. 6 is a block diagram illustrating the configuration of a conventional active noise control system.

Now, referring to FIGS. 4 and 5, a description is made to the microphone monitor 28 monitoring the ratio between the duration of the positive sign of the error signal "e" and that of the negative sign thereof.

FIG. 4 graphically shows an exemplary sequence {e(n)} of error signals "e" that are quantized at sampling cycle Ts (sec) intervals from time "0" (n=0) at which the A-D converter 8 starts operating after the active noise control system has been activated. The microphone monitor 28 is provided therein with a (up-count) counter to measure the duration from the point in time of a change in sign of the error signal "e" to the subsequent change. The counter clears the initial value to zero at n=0. Thereafter, at the initial stage of each sampling cycle of n=1, 2, 3 and so on, the counter is incremented by one.

Now, the microphone monitor 28 compares the sign of the error signal "e" during the current sampling interval with that of the error signal "e" during the previous sampling interval. If the signs are different, the microphone monitor 28 performs the following three steps. Initially, the process calculates the ratio between the current counter value and the previously stored counter value to determine the ratio between the duration of the most recent positive sign of the error signal "e" and that of the most recent negative sign thereof. Then, for use in the next ratio calculation, the process stores the current counter value. Finally, the process clears the counter to zero in order to measure the duration of the currently changed sign of the error signal "e."

It is to be understood that the ratio to be determined is calculated as follows. That is, the current counter value and the previously stored counter value are compared to each other, based on the smaller value of which the ratio is calculated. At the end of each sampling cycle, the microphone monitor 28 compares the ratio determined as described above with a value that has been set to sense an abnormal level to determine whether the error signal "e" is normal. At this stage, it should be noted that the ratio which is determined using a counter value for measuring duration (t1) from n=0 in which the sign of the error signal "e" changes for the first time is invalid. This is because an error signal having the same sign as that of error signal e(0) may conceivably exist before n=0 at which the A-D converter 8 is activated.

Considering the points discussed above, the microphone monitor 28 does not properly sense the abnormal level of the error signal "e" before the ratio is calculated for the first time or while the counter value for measuring t1 is used for the calculation of the ratio. In other words, the microphone monitor 28 properly senses the abnormal level of the error signal "e" only after the ratio is calculated three times. Therefore, until the ratio is calculated three times, the error signal "e" is always to be determined normal. The process thus starts using the value of a determined ratio to sense the abnormal level at the point in time at which the ratio is calculated for the third or subsequent times. Suppose that the error signal "e" indicates an abnormal level for some reason and the ratio is greater than or equal to a setting. In this case, since the duration of the positive sign of the error signal "e" and that of the negative sign thereof are significantly different from each other, the process senses the abnormal level indicative of a DC offset.

The example shown in FIG. 4 is designed such that the microphone monitor 28 senses the abnormal level when the ratio between the duration of the positive sign of the error signal "e" and that of the negative sign thereof is seven or greater. Initially, at n=0, the microphone monitor 28 stores the sign of error signal e(0) being negative, while the counter is cleared to zero. At n=1, the counter is incremented, while the sign of error signal e(1) during the current sampling interval is compared with that of the error signal e(0) during the previous sampling interval. Since the sign of e(1) is negative or the same as the sign of e(0) and the ratio has not yet been calculated for the first time, the error signal "e" is determined normal. Subsequently in the similar manner, at n=2 and 3, since the sign of the error signal "e" remains unchanged and the ratio has not yet been calculated for the first time, the error signal "e" is thus determined normal during these intervals.

Now, at n=4, the sign of error signal e(4) has changed from negative to positive for the first time. At this stage, the counter has been incremented at the initial stage of the sampling cycle to a current value of 4, indicating that t1=4×Ts (sec). Since the sign of the error signal "e" has been changed, the ratio is calculated using the aforementioned current counter value. The current counter value of 4 and a previous counter value (an appropriate value of 2 is prepared here as the previous counter value) are compared with each other, based on the smaller value of which (in this case, the previous counter value 2) the ratio is calculated. That is, a value of 4/2=2 is the ratio determined. However, this value is invalid as described above, and not used for sensing the abnormal level.

Then, the current counter value is stored for use in the next calculation of the ratio. Furthermore, to measure later the duration in which the sign of the error signal "e" is positive, the counter is cleared to zero. Since the ratio has been currently calculated for the first time but its value is neglected, the error signal "e" is determined normal. Subsequently, at n=5, 6, 7, and 8, since the positive sign of the error signal "e" remains unchanged and the ratio is not calculated, the error signal "e" is determined normal during these intervals. Now, the sign of the error signal "e" changes at n=9. At this stage, the sign of error signal e(9) changes from positive to negative for the second time. At this stage, the counter has been incremented at the initial stage of the sampling cycle to a current value of 5, indicating that $t_2$=5×Ts (sec). Since the sign of the error signal "e" has been changed, the ratio is first calculated using the aforementioned current counter value. The current counter value of 5 and the previous counter value of 4 are compared with each other, based on the smaller value of which (in this case, the previous counter value of 4) the ratio is calculated. That is, a value of 5/4=1.25 is the ratio determined. However, this value is invalid as described above, and not used for sensing the abnormal level.

Then, the current counter value is stored for use in the next calculation of the ratio. Furthermore, to measure later the duration in which the sign of the error signal "e" is negative, the counter is cleared to zero. Since the ratio has been currently calculated for the second time but its value is neglected, the error signal "e" is determined normal. Subsequently, at n=10, 11, . . . , 15, and 16, since the negative sign of the error signal "e" remains unchanged and the ratio is not calculated, the error signal "e" is determined normal during these intervals. Now, the sign of the error signal "e" changes at n=17. At this stage, the sign of error signal e(17) changes from negative to positive for the third time. At this stage, the counter has been incremented at the initial stage of the sampling cycle to a current value of 8, indicating that t3=8×Ts (sec). Since the sign of the error signal "e" has been changed, the ratio is first calculated using the aforementioned current counter value. The current counter value of 8 and the previous counter value of 5 are compared with each other, based on the smaller value of which (in this case, the previous counter value of 5) the ratio is calculated. That is, a value of 8/5=1.6 is the ratio determined.

Next, the current counter value is stored for use in the next calculation of the ratio. Furthermore, to measure later the duration in which the sign of the error signal "e" is positive, the counter is cleared to zero. Since the ratio has been currently calculated for the third time, the determined ratio of 1.6 is used to determine whether the error signal "e" is normal. Subsequently, determined ratios are all employed as valid values to sense the abnormal level of the error signal "e." The currently determined ratio of 1.6 is less than a setting of 7 for sensing the abnormal level. Therefore, the microphone monitor 28 determines that the error signal "e" is normal.

Then, the sign of the error signal "e" changes at n=18. At this stage, the sign of error signal e(18) changes from positive to negative for the fourth time. At this stage, the counter has been incremented at the initial stage of the sampling cycle to a current value of 1, indicating that t4=1×Ts (sec). Since the sign of the error signal "e" has been changed, the ratio is first calculated using the aforementioned current counter value. The current counter value of 1 and the previous counter value of 8 are compared with each other, based on the smaller value of which (in this case, the current counter value of 1) the ratio is calculated. That is, a value of 8/1=8 is the ratio determined.

Then, the current counter value is stored for use in the next calculation of the ratio. Furthermore, to measure later the duration in which the sign of the error signal "e" is positive, the counter is cleared to zero. The currently determined ratio of 8 is greater than a setting of 7 for sensing the abnormal level. At this time, the microphone monitor 28 determines that the duration of the positive sign of the error signal "e" and that of the negative sign thereof are significantly different from each other, sensing the abnormal level indicative of a DC offset.

FIG. 5 is a flowchart showing the microphone monitor 28 operating at every sampling cycle. First, at step s21, the counter value is incremented. Then, in step s22, the process determines the current sign of the error signal "e." If the current sign of the error signal "e" is negative, the process determines in step s23 whether the sign of the error signal "e" during the previous sampling interval is also negative. If the sign of the error signal "e" during the previous sampling interval is also negative, the sign of the error signal "e" has been successively negative, and thus no processing, such as a ratio calculation, is performed. If the sign of the error signal "e" during the previous sampling interval is positive, the sign of the error signal "e" has changed from positive to negative, and thus the process calculates in step s24 the ratio between the current counter value and the previously stored counter value.

Next, in step s25, the current counter value is stored for use in the next calculation of the ratio. Furthermore, to measure later the duration, the counter is cleared to zero in step s26. Then, for use during the next sampling interval, the current sign of the error signal "e" being negative is stored in step s27. Likewise, if the current sign of the error signal "e" determined in step s22 is positive, the process determines in step s28 whether the sign of the error signal "e" during the previous sampling interval is also positive. If the sign of the error signal "e" during the previous sampling interval is also positive, the sign of the error signal "e" has been successively positive, and thus no processing, such as a ratio calculation, is performed. If the sign of the error signal "e" during the previous sampling interval is negative, the sign of the error signal "e" has changed from negative to positive, and thus the process calculates in step s29 the ratio between the current counter value and the previously stored counter value.

Then, in step s30, the current counter value is stored for use in the next calculation of the ratio. Furthermore, to measure later the duration, the counter is cleared to zero in step s31. Then, for use during the next sampling interval, the current sign of the error signal "e" being positive is stored in step s32. Now, the process determines in step s33 whether the ratio is calculated at steps s24 and s29 for the third or subsequent times. If the ratio is calculated for the second or preceding times, the process determines in step s37 that the error signal "e" is normal. If the ratio is calculated for the third or subsequent times, the process determines in step s34 whether the determined ratio is greater than or equal to the setting for sensing the abnormal level. If the determined ratio is less than the setting, the process determines in step s36 that the error signal "e" is normal. If the determined ratio is greater than or equal to the setting, the process senses the abnormal level in step s35, and the microphone monitor 28 interrupts the switch 29.

As described above, the active noise control system according to the second embodiment is designed such that the duration of the positive sign of the error signal from the microphone 5 employed for adaptive computations and that of the negative sign thereof are each measured to determine the ratio therebetween. If the ratio is greater than or equal to a setting, the process senses the abnormal level of the error signal having a DC offset to then stop the secondary noise from being generated. This prevents the user from hearing an abnormal output acoustic noise from the adaptive controller 27.

Although the present invention has been fully described in connection with the preferred embodiment thereof, it is to be noted that various changes and modifications apparent to those skilled in the art are to be understood as included within the scope of the present invention as defined by the appended claims unless they depart therefrom.

What is claimed is:

1. An active noise control system comprising:

an adaptive controller for computing an amplitude and a phase of a secondary noise which actively cancels a primary noise generated in a passenger compartment;

secondary noise generator for producing said secondary noise in the passenger compartment;

a microphone for sensing a residual noise resulting from the interference of said secondary noise with said primary noise; and microphone monitor for stopping said secondary noise being produced from said adaptive controller when output signals delivered by said microphone to be supplied to said adaptive controller have the same positive or negative sign for a predetermined duration.

2. An active noise control system comprising:

an adaptive controller for computing an amplitude and a phase of a secondary noise which actively cancels a primary noise generated in a passenger compartment;

secondary noise generator for producing said secondary noise in the passenger compartment;

a microphone for sensing a residual noise resulting from the interference of said secondary noise with said primary noise; and microphone monitor for stopping said secondary noise being produced from said adaptive controller when a ratio between a duration of the positive sign of output signals delivered by said microphone to be supplied to said adaptive controller and that of the negative sign thereof is greater than or equal to a predetermined value.

* * * * *